US009915814B2

United States Patent
Ueno et al.

(10) Patent No.: US 9,915,814 B2
(45) Date of Patent: Mar. 13, 2018

(54) FLUORESCENCE OBSERVATION UNIT AND FLUORESCENCE OBSERVATION APPARATUS

(71) Applicant: OLYMPUS CORPORATION, Shibuya-ku, Tokyo (JP)

(72) Inventors: Makio Ueno, Nagano (JP); Masahito Dohi, Tokyo (JP); Atsuhiro Tsuchiya, Tokyo (JP); Hiroyasu Hebiishi, Tokyo (JP)

(73) Assignee: Olympus Corporation, Tokyo (JP)

( * ) Notice: Subject to any disclaimer, the term of this patent is extended or adjusted under 35 U.S.C. 154(b) by 175 days.

(21) Appl. No.: 15/060,585

(22) Filed: Mar. 3, 2016

(65) Prior Publication Data

US 2016/0274345 A1  Sep. 22, 2016

(30) Foreign Application Priority Data

Mar. 19, 2015 (JP) ................. 2015-056294

(51) Int. Cl.
*G02B 21/00* (2006.01)
*G02B 21/36* (2006.01)
(Continued)

(52) U.S. Cl.
CPC ........ *G02B 21/0076* (2013.01); *A61B 5/0059* (2013.01); *A61B 5/0062* (2013.01);
(Continued)

(58) Field of Classification Search
CPC .............. G02B 21/0076; G02B 21/361; G02B 27/0025; G02B 21/0032; G02B 21/0084;
(Continued)

(56) References Cited

U.S. PATENT DOCUMENTS

2004/0004194 A1   1/2004 Amblard et al.
2005/0187441 A1   8/2005 Kawasaki et al.
(Continued)

FOREIGN PATENT DOCUMENTS

EP   1207387 A1   5/2002
JP   2005202338 A   7/2005
(Continued)

OTHER PUBLICATIONS

Extended European Search Report dated Jun. 14, 2016, issued in counterpart European Application No. 16159376.9.
(Continued)

*Primary Examiner* — Tony Ko
(74) *Attorney, Agent, or Firm* — Holtz Holtz & Volek PC

(57) ABSTRACT

A fluorescence observation unit includes a scanner that scans ultrashort pulsed laser light, a pupil projection lens that focuses the scanned ultrashort pulsed laser light, an image-forming lens that converts the focused ultrashort pulsed laser light to substantially collimated light and causes the ultrashort pulsed laser light to be incident on the objective lens, and a dichroic mirror that splits off, from the optic path of the ultrashort pulsed laser light, fluorescence generated in a sample due to irradiation with the ultrashort pulsed laser light and collected by the objective lens. The image-forming lens includes a first optical system having positive refractive power, and a second optical system having negative refractive power and disposed at a position closer to the scanner than the first optical system is. The dichroic mirror is disposed between the first optical system and the second optical system.

13 Claims, 6 Drawing Sheets

(51) Int. Cl.
    *G02B 27/14*   (2006.01)
    *G02B 27/00*   (2006.01)
    *G01N 21/64*   (2006.01)
    *A61B 5/00*    (2006.01)

(52) U.S. Cl.
    CPC ..... *G01N 21/6402* (2013.01); *G01N 21/6458* (2013.01); *G01N 21/6486* (2013.01); *G02B 21/0032* (2013.01); *G02B 21/0084* (2013.01); *G02B 21/361* (2013.01); *G02B 27/0025* (2013.01); *G02B 27/141* (2013.01)

(58) Field of Classification Search
    CPC ... G02B 27/141; A61B 5/0062; A61B 5/0059; G01N 21/6402; G01N 21/6486; G01N 21/6458
    See application file for complete search history.

(56) References Cited

U.S. PATENT DOCUMENTS

| | | |
|---|---|---|
| 2005/0237604 A1 | 10/2005 | Kawano et al. |
| 2005/0279950 A1 | 12/2005 | Kawano et al. |
| 2007/0047071 A1 | 3/2007 | Honda et al. |
| 2015/0177502 A1* | 6/2015 | Matsukawa ........ G02B 21/0032 348/79 |
| 2017/0123196 A1* | 5/2017 | Svoboda ............ G02B 21/0032 |
| 2017/0205611 A1* | 7/2017 | Fukuyama ........... G02B 21/008 |
| 2017/0269000 A1* | 9/2017 | Kaneko ............. G01N 21/6458 |

FOREIGN PATENT DOCUMENTS

| | | |
|---|---|---|
| JP | 2005300655 A | 10/2005 |
| JP | 2005300665 A | 10/2005 |
| JP | 2006272416 A | 10/2006 |
| JP | 2007057766 A | 3/2007 |
| JP | 2008197127 A | 8/2008 |
| JP | 4276971 B2 | 6/2009 |

OTHER PUBLICATIONS

Stelzer, "The Intermediate Optical System of Laser-scanning Confocal Mircoscopes", Handbook of Biological Confocal Microscopy, Aug. 1, 1989, pp. 93-103.

* cited by examiner

FLUORESCENCE OBSERVATION UNIT AND FLUORESCENCE OBSERVATION APPARATUS

CROSS-REFERENCE TO RELATED APPLICATIONS

This application is based on Japanese Patent Application No. 2015-056294 filed on Mar. 19, 2015, the content of which is incorporated herein by reference.

TECHNICAL FIELD

The present invention relates to a fluorescence observation unit and a fluorescence observation apparatus.

BACKGROUND ART

In the related art, there is a known observation apparatus for observing a living sample, such as a small laboratory animal, with which observation is performed by disposing an objective lens in various directions or at various positions with respect to the sample (for example, see PTL 1).

In this observation apparatus disclosed in PTL 1, fluorescence generated at a light-focusing position due to a multiphoton excitation effect by focusing ultrashort pulsed laser light on a specimen is split off from the optical path of the ultrashort pulsed laser light immediately behind the objective lens, is guided to an external photodetector by an optical fiber, and is detected. By using a multiphoton-excitation-type observation apparatus like this, it is possible to focus the ultrashort pulsed laser light at a portion deep inside the sample, thus generating fluorescence, whereby it is possible to acquire a fluorescence image of the portion deep inside the sample.

In the case of the multiphoton-excitation-type observation apparatus, the fluorescence collected by the objective lens is split off immediately behind the objective lens, before returning to the scanner. Hence, when ultrashort pulsed laser light is scanned over the sample by the scanner, the position of a fluorescence beam also varies accordingly. Hence, in the case in which the scanning area scanned by the scanner is large, it is difficult to make the split-off fluorescence enter an optical fiber.

Furthermore, when the sample is a scattering material, such as a biological tissue, the fluorescence generated at the light-focusing position of the ultrashort pulsed laser light is scattered by the sample in the course of returning to the objective lens. In order to obtain a bright fluorescence image, it is necessary that fluorescence collected from a wide area of the sample by using the objective lens is detected.

CITATION LIST

Patent Literature

{PTL 1} Japanese Unexamined Patent Application, Publication No. 2005-300655

SUMMARY OF INVENTION

A first aspect of the present invention is a fluorescence observation unit including: a scanner that scans ultrashort pulsed laser light from a light source; a pupil projection lens that focuses the ultrashort pulsed laser light scanned by the scanner; an image-forming lens that converts the ultrashort pulsed laser light, focused by the pupil projection lens, to substantially collimated light and causes the ultrashort pulsed laser light to be incident on an objective lens; and a dichroic mirror that splits off, from the optical path of the ultrashort pulsed laser light, fluorescence that is generated at a light-focusing position as a result of the ultrashort pulsed laser light being focused on a sample by the objective lens and is collected by the objective lens. The image-forming lens includes a first optical system having positive refractive power and disposed adjacent to the objective lens, and a second optical system having negative refractive power and disposed at a position closer to the pupil projection lens than the first optical system is. The dichroic mirror is disposed between the first optical system and the second optical system.

A second aspect of the present invention is a fluorescence observation apparatus including: the fluorescence observation unit according to the first aspect; and a photodetector that detects the fluorescence split off by the dichroic mirror.

DESCRIPTION OF EMBODIMENTS

A fluorescence observation unit 3 and a fluorescence observation apparatus 1 according to an embodiment of the present invention will be described below with reference to the drawings.

Figure 1:
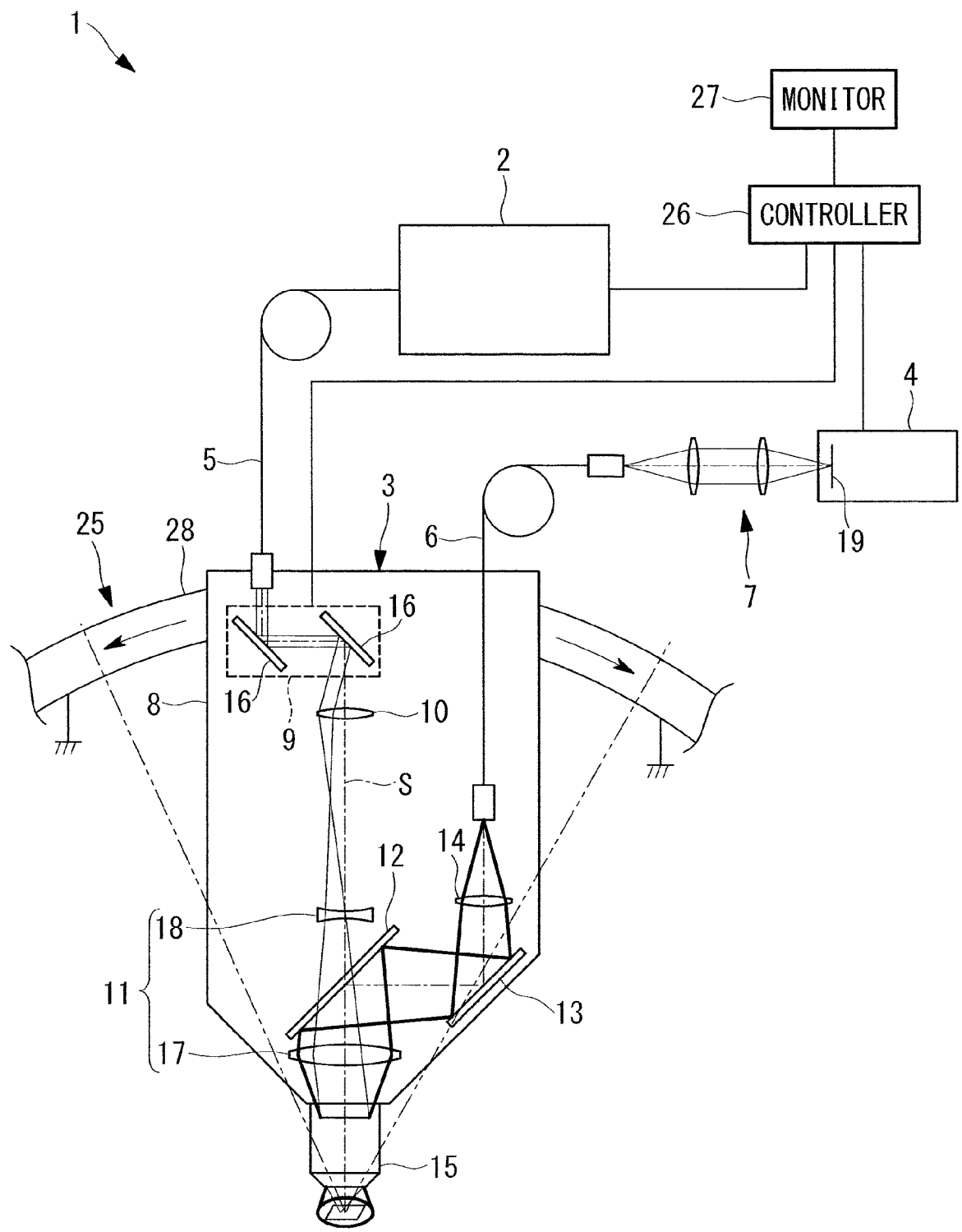
FIG. 1 illustrates a schematic diagram of the overall configuration of a fluorescence observation apparatus according to an embodiment of the present invention.

As shown in FIG. 1, the fluorescence observation apparatus 1 according to this embodiment is a multiphoton-excitation laser scanning microscope and includes a light source 2 that emits ultrashort pulsed laser light in a near-infrared band; a fluorescence observation unit 3, according to this embodiment, that irradiates a sample X with the ultrashort pulsed laser light emitted from the light source and collects fluorescence generated in the sample X; a photomultiplier tube (photodetector) 4 that detects the fluorescence collected by the fluorescence observation unit 3; a first optical fiber (light-source optical fiber) 5 connecting the light source 2 and the fluorescence observation unit 3; a second optical fiber (optical fiber) 6 for guiding the fluorescence from the fluorescence observation unit 3 to the photomultiplier tube 4; a relay optical system (relay lens) 7;

a swiveling mechanism 25 that can swivel the fluorescence observation unit 3; a controller 26 that inputs movement instructions to the light source 2 and the fluorescence observation unit 3; and a monitor 27.

The fluorescence observation unit 3 includes a housing 8; and a scanner 9, a pupil projection lens 10, an image-forming lens 11, a dichroic mirror 12, a mirror (optical-path deflecting member) 13, and a coupling lens 14, which are accommodated in the housing 8.

Furthermore, an objective lens 15 is replaceably mounted to the fluorescence observation unit 3.

The scanner 9 is, for example, a so-called proximity galvanometer mirror, which includes two galvanometer mirrors 16 that are caused to swivel about non-parallel axes. The scanner 9 can two-dimensionally scan the ultrashort pulsed laser light emitted from the light source 2 and guided by the first optical fiber 5.

The pupil projection lens 10 focuses the ultrashort pulsed laser light scanned by the scanner 9 to form an intermediate image.

The image-forming lens 11 converts the ultrashort pulsed laser light, with which the pupil projection lens 10 has formed the intermediate image, into substantially collimated light and causes the light to enter the objective lens 15.

In this embodiment, the image-forming lens 11 includes a first optical system 17 having positive refractive power and a second optical system 18 having negative refractive power. The first optical system 17 is disposed adjacent to the base end of the objective lens 15. The second optical system 18 is disposed at a position closer to the pupil projection lens 10 than the first optical system 17 is, so as to be spaced from the first optical system 17 in the optical axis S direction.

In the drawings, although the first optical system 17 and the second optical system 18 are each illustrated as being formed of a single lens, the configurations of the optical systems 17 and 18 are not limited thereto, and they may be each formed by combining a plurality of lenses so as to have positive refractive power or negative refractive power as a whole.

Specifically, the diverging ultrashort pulsed laser light entering the image-forming lens 11 from the pupil projection lens 10 diverges further as it passes through the second optical system 18, is focused and converted to substantially collimated light as it passes through the first optical system 17, and enters the objective lens 15.

The dichroic mirror 12 is formed in the shape of a parallel flat plate and is disposed at an angle of, for example, 45° with respect to the optical axis S. The dichroic mirror 12 has such transmittance characteristics that it allows the ultrashort pulsed laser light to pass therethrough, while deflecting the fluorescence entering from the objective lens 15 by substantially 90° to split the fluorescence off from the optical path of the ultrashort pulsed laser light.

The mirror 13 bends the optical path of the fluorescence such that the fluorescence split by the dichroic mirror 12 is further deflected by substantially 90° and is directed toward the opposite side of the objective lens 15, along the direction parallel to the optical axis S of the objective lens 15.

The coupling lens 14 further focuses the fluorescence deflected by the mirror 13 and makes the fluorescence enter an incident end of the second optical fiber 6.

The first optical fiber 5 is, for example, a single-mode fiber.

The second optical fiber 6 is a multi-mode fiber, and, in particular, is preferably a liquid fiber. The core diameter, at the exit end, of the second optical fiber 6 is less than or equal to the effective diameter of the photomultiplier tube 4.

The relay optical system 7 temporarily converts the diverging fluorescence, propagated by the second optical fiber 6 and emitted from the exit end, to substantially collimated light, focuses the fluorescence again, and causes it to be incident on a photoelectric conversion surface 19 of the photomultiplier tube 4. The projection magnification of the relay optical system 7 from the exit end of the second optical fiber 6 to the photoelectric conversion surface 19 of the photomultiplier tube 4 is set such that the diameter of the fluorescence beam entering the photomultiplier tube 4 is within the effective area of the photoelectric conversion surface 19 of the photomultiplier tube 4 and such that the incident NA to the photomultiplier tube 4 is within an allowable range of the photomultiplier tube 4. The preferred relay magnification of the relay optical system 7 is, for example, 1×.

The swiveling mechanism 25 includes a slider (not shown) to which the housing 8 of the fluorescence observation unit 3 is fixed, and a circular arc shaped rail 28 for guiding the slider. The rail 28 has a circular arc shape centered on the focal position of the objective lens 15*a* or the vicinity thereof. By moving the slider over the rail 28, the fluorescence observation unit 3 can be swiveled about the axis located at the focal position of the objective lens 15 or the vicinity thereof.

The controller 26 includes a computer (not shown) that executes a control program for the light source 2 and the scanner 9 of the fluorescence observation unit 3, a memory (not shown) storing the control program executed by the computer, and an interface unit (not shown). The computer generates a two-dimensional image on the basis of the information about the position scanned by the scanner 9 according to the executed control program and the brightness signal detected by the photomultiplier tube 4. The memory stores the two-dimensional image generated by the computer.

The interface unit includes a driver that transmits an operation instruction from the computer to the scanner 9 and a signal processing circuit that converts the signal detected by the photomultiplier tube 4 from analog to digital and transmits the signal to the computer.

The monitor 27 displays the two-dimensional image generated by the computer.

The operation of the fluorescence observation unit 3 and fluorescence observation apparatus 1 according to this embodiment, configured as above, will be described below.

When a fluorescence image of a relatively deep portion in the sample X is to be acquired using the fluorescence observation apparatus 1 according to this embodiment, ultrashort pulsed laser light is generated by the light source 2, in response to the operation instruction from the controller 26. The ultrashort pulsed laser light generated by the light source 2 is guided to the fluorescence observation unit 3 via the first optical fiber 5.

The ultrashort pulsed laser light entering the fluorescence observation unit 3 through the first optical fiber 5 is two-dimensionally scanned by the scanner 9 according to the operation instruction from the controller 26 transmitted via the driver, is focused by the pupil projection lens 10, is converted into substantially collimated light by the image-forming lens 11, and then enters the objective lens 15. The ultrashort pulsed laser light focused at the focal position of the objective lens 15 increases the photon density in a very limited area near the focal position and excites a fluorescent substance existing in that area to cause fluorescence to be generated.

Figure 2:
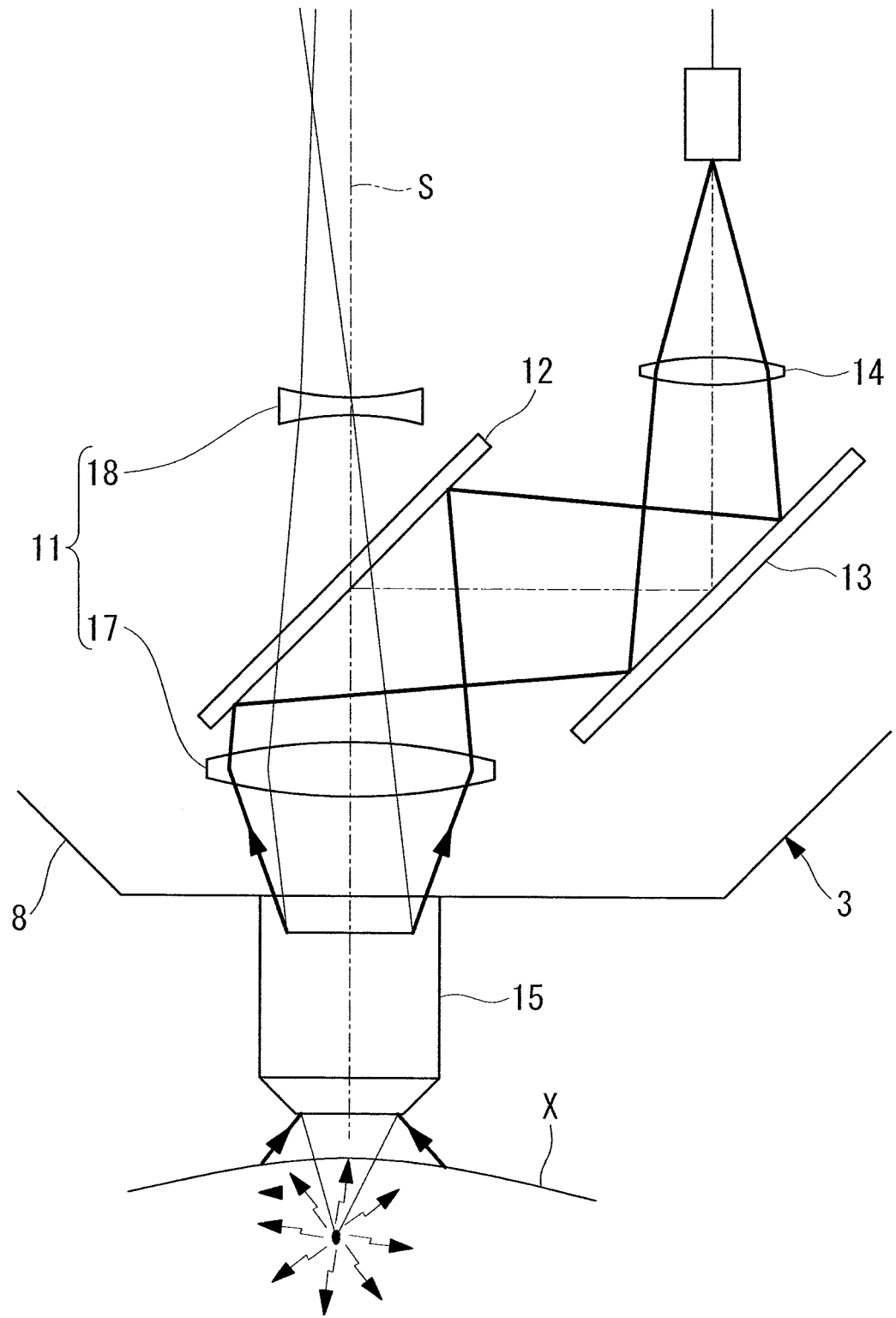
FIG. 2 illustrates a partial enlarged view of FIG. 1 for explaining detection of fluorescence by a fluorescence observation unit provided in the fluorescence observation apparatus in FIG. 1.

The generated fluorescence is radiated in all directions, as shown in FIG. 2, and is scattered within the sample X. Of this scattered fluorescence, the fluorescence radiated from the surface of the sample X toward the objective lens 15 is collected by the objective lens 15.

In this case, with the fluorescence observation unit 3 according to this embodiment, because the image-forming lens 11 in which the first optical system 17 having positive refractive power and the second optical system 18 having negative refractive power are arranged at a distance from each other in the optical axis S direction is employed, an advantage is obtained that it is possible to reduce the rear-side focal length and to make the image-forming lens 11 itself have a compact configuration, unlike the case of the typical microscope, where a convex-concave doublet lens is used as the image-forming lens 11.

Furthermore, because the fluorescence is split off by the dichroic mirror 12 that is disposed between the first optical system 17 and the second optical system 18, it is possible to split off the fluorescence that is focused with a strong refractive power, compared with a case where the fluorescence passing through the whole image-forming lens 11 is split off.

Specifically, the fluorescence generated at the focal position of the ultrashort pulsed laser light spreads around the focal position due to scattering inside the surrounding sample X. Because the spread fluorescence is also generated in the focal position of the ultrashort pulsed laser light, it is desirable to collect as much fluorescence as possible.

As shown in FIG. 2, when the ultrashort pulsed laser light is focused at each position in the scanning range of the ultrashort pulsed laser light, scattered fluorescence enters the objective lens 15 from a wider area including the scanning range. The light entering the objective lens 15 from a wide area like this is collected by the objective lens 15 and then diverges toward the image-forming lens 11. Because the first optical system 17 disposed in the vicinity of the objective lens 15 has higher positive refractive power than a typical image-forming lens, the light enters a narrow area of the dichroic mirror 12, in the form of converging light the central axis of which coincides with the optical axis S of the objective lens 15. Thus, even when the dichroic mirror 12 is small, it is possible to split off the fluorescence coming from a wide area of the sample X from the optical path of the ultrashort pulsed laser light.

More specifically, it is possible to collect off-axis fluorescence emitted from the objective lens 15 toward the image-forming lens 11 at a large angle with respect to the optical axis S by deflecting, with the first optical system 17, the fluorescence in the direction parallel to the optical axis S and to guide the fluorescence to the photomultiplier tube 4.

As a result, with the fluorescence observation unit 3 and fluorescence observation apparatus 1 according to this embodiment, it is possible to efficiently collect the fluorescence generated at the focal position of the ultrashort pulsed laser light.

The fluorescence split off by the dichroic mirror 12 is deflected by the mirror 13, is further focused by the coupling lens 14, and is made to enter the second optical fiber 6.

Because the second optical fiber 6 is made of a multi-mode fiber, in particular, a liquid fiber, the core of the optical fiber 6 is large. Thus, it is possible to make the fluorescence focused by the coupling lens 14 efficiently enter the second optical fiber 6.

Specifically, with the fluorescence observation unit 3 according to this embodiment that causes the fluorescence coming from a wider area beyond the scanning range of the scanner 9 to be constantly incident on the second optical fiber 6, even when the ultrashort pulsed laser light is scanned by the scanner 9, the fluorescence entering the second optical fiber 6 does not fluctuate and can be made to efficiently enter the second optical fiber 6.

The fluorescence guided by the second optical fiber 6 is emitted from the exit end of the second optical fiber 6, is relayed by the relay optical system 7, and is incident on the photoelectric conversion surface 19 of the photomultiplier tube 4, where it is detected as a brightness signal. The detected brightness signal is converted from analog to digital by the signal processing circuit and is transmitted to the computer. The computer generates a two-dimensional image on the basis of the transmitted brightness signal and the information about the position scanned by the scanner 9, and the generated two-dimensional image is stored in the memory. As a result, it is possible to display the two-dimensional image stored in the memory on the monitor 27 as necessary and to observe the fluorescence of the sample X.

Furthermore, the relay magnification of the relay optical system 7 is set such that the core diameter, at the exit end, of the second optical fiber 6 is projected within the this case, by setting the relay magnification of the relay optical system 7 as viewed from the photomultiplier tube 4 side to substantially 1× or less, the inclination of the fluorescence entering the photoelectric conversion surface 19 is reduced, which is advantageous for preventing a decrease in intensity of detected light due to the angular dependence of the detection sensitivity.

Furthermore, because the core diameter, at the exit end, of the second optical fiber 6 is less than or equal to the effective diameter of the photomultiplier tube 4, all of the fluorescence guided by the second optical fiber 6 is incident on the photoelectric conversion surface 19 of the photomultiplier tube 4. Thus, it is possible to efficiently detect the fluorescence, without being influenced by the entrance position dependence.

Furthermore, in this embodiment, because the fluorescence deflected by 90° by the dichroic mirror 12 is further deflected by 90° by the mirror 13, it is possible to easily make the fluorescence, focused by the coupling lens 14, enter the second optical fiber 6 fixed to the housing 8 so as to extend in the direction substantially parallel to the optical axis S of the objective lens 15.

Furthermore, in this embodiment, even when the fluorescence observation unit 3 is swiveled by the swiveling mechanism 25 for causing the fluorescence observation unit 3 to swivel about the axis at the focal position of the objective lens 15 or the vicinity thereof, the second optical fiber 6 does not inhibit such a movement, and it is possible to make the space around the objective lens 15 more compact, ensuring a large swiveling angle.

Figure 3:
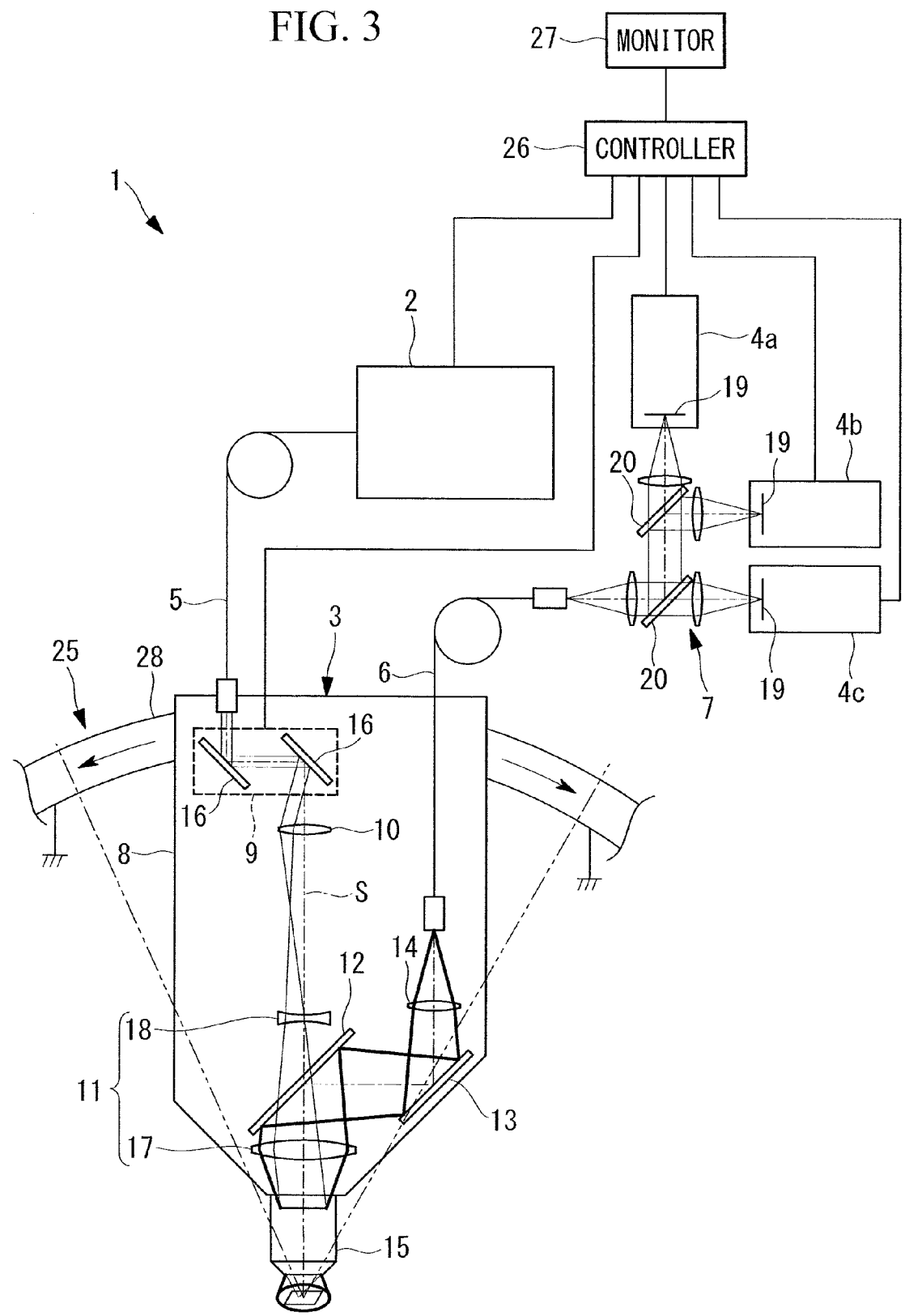
FIG. 3 illustrates a schematic diagram of the overall configuration of a first modification of the fluorescence observation apparatus in FIG. 1 for detecting multiple-wavelength fluorescence.

Although the case where single-wavelength fluorescence is acquired has been described in this embodiment, when multi-wavelength fluorescence is acquired simultaneously, as shown in FIG. 3, dichroic mirrors (light-splitting dichroic mirrors) 20 may be disposed in the optical path of the collimated light formed by the relay optical system 7 to split the fluorescence according to the wavelengths and to detect the split-off fluorescences with separate photomultiplier tubes 4a, 4b, and 4c.

Figure 4:
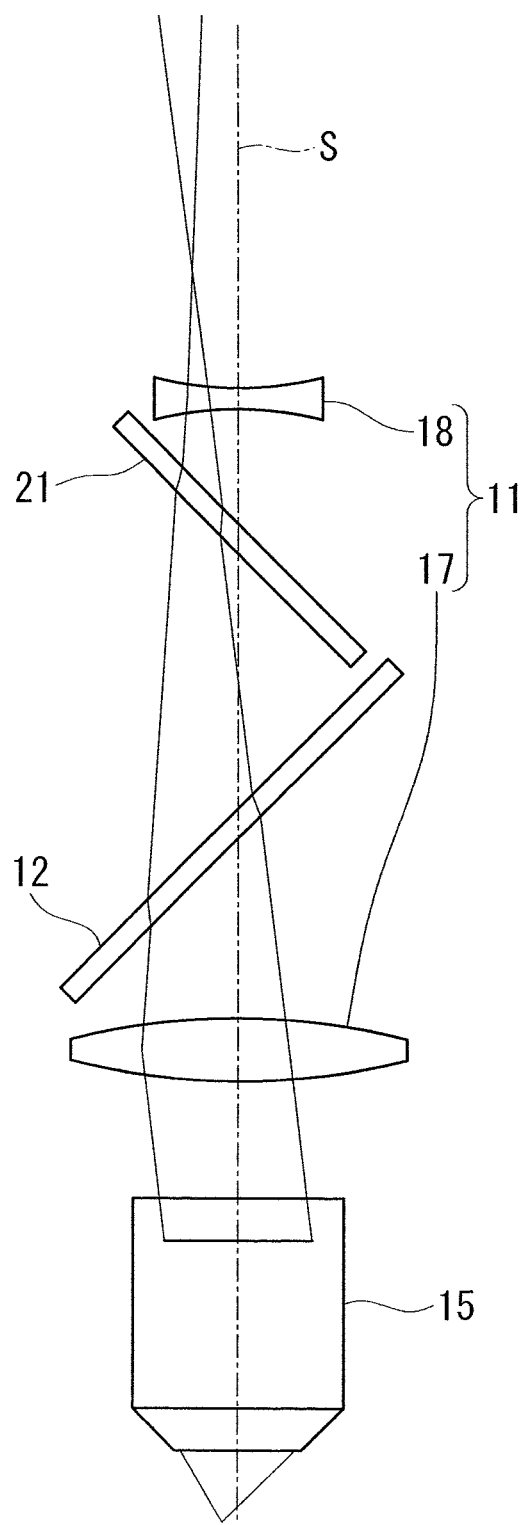
FIG. 4 illustrates a second modification of the fluorescence observation apparatus in FIG. 1, and illustrates a diagram for explaining the effect of an astigmatism correcting plate.

In this embodiment, because the dichroic mirror 12, formed of a parallel flat plate, is disposed between the first optical system 17 and the second optical system 18, the ultrashort pulsed laser light passing through the dichroic mirror 12 is refracted as it passes through the dichroic mirror 12 and is shifted (astigmatism) in the direction in which the dichroic mirror 12 is inclined. To counter this problem, as shown in FIG. 4, an astigmatism correcting plate 21, which is formed of a glass parallel flat plate having the same thickness as the dichroic mirror 12 and inclined by the same angle as the dichroic mirror 12 but in the opposite direction, may be provided. By doing so, it is possible to prevent a shift in focal position of the ultrashort pulsed laser light due to the dichroic mirror 12.

Figure 5:
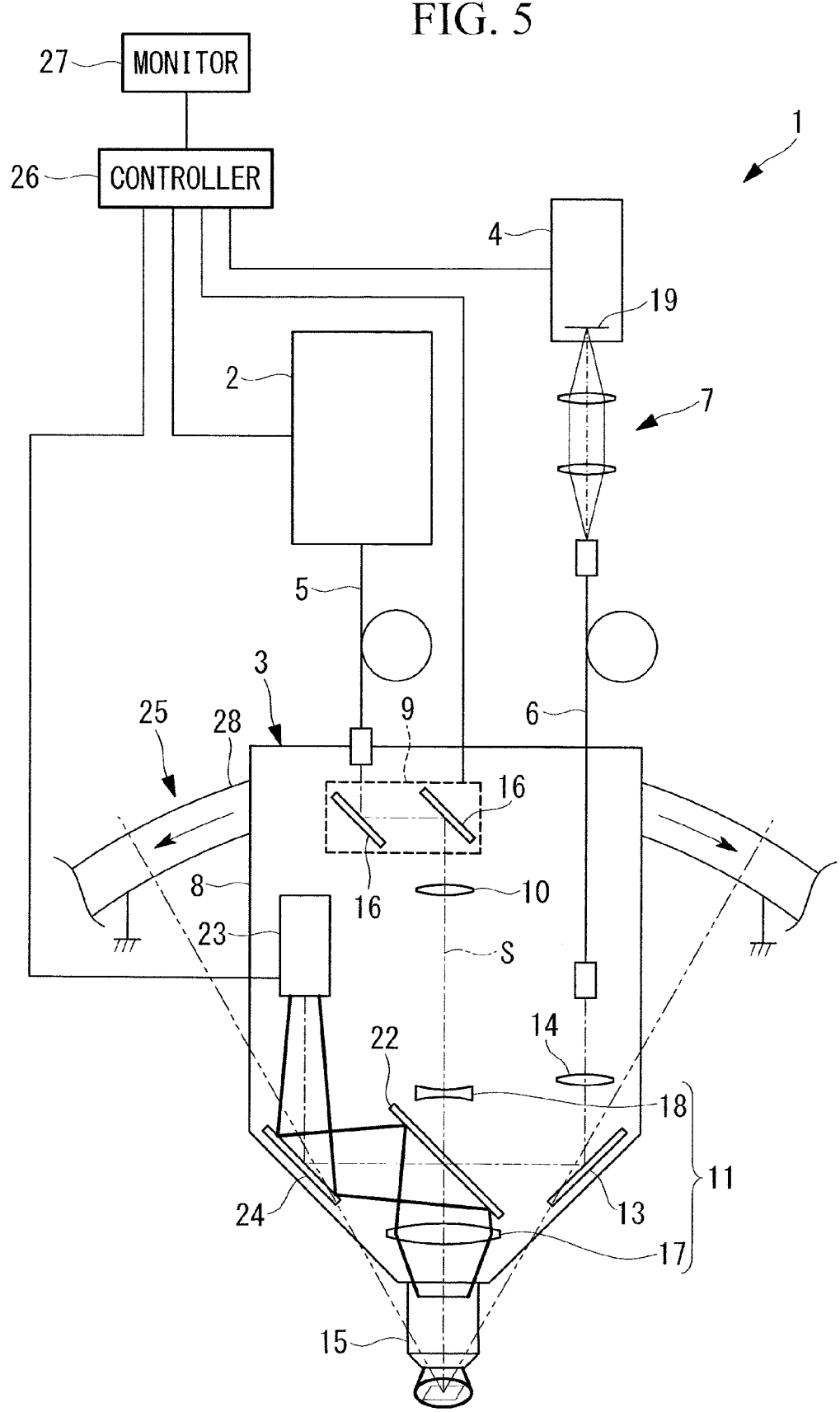
FIG. 5 illustrates a schematic diagram of the overall configuration of a third modification of the fluorescence observation apparatus in FIG. 1 having a mechanism for observing the surface of a sample.
Figure 6:
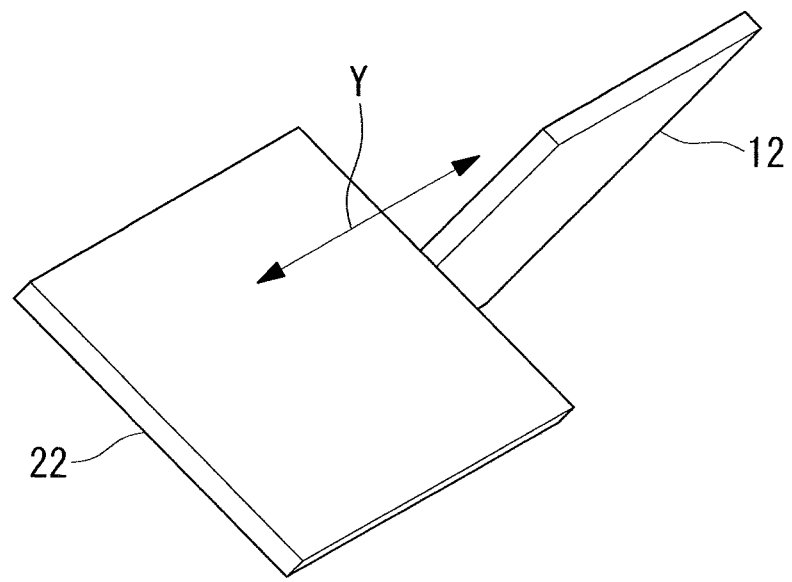
FIG. 6 illustrates a perspective view for explaining an insertion/retraction operation of a dichroic mirror and a mirror provided in the fluorescence observation apparatus in FIG. 5.

In this embodiment, as shown in FIG. 6, a mirror (observation-light deflecting member) 22 inclined in a direction different from the direction in which the dichroic mirror 12 is inclined may be provided, and an insertion/retraction mechanism (not shown) that moves the dichroic mirror 12 and the mirror 22 in a direction as indicated by an arrow Y to alternatively dispose the mirrors 12 and 22 on the optical axis S of the objective lens 15 may be provided. The insertion/retraction mechanism is, for example, a linear motion mechanism. In this case, as shown in FIG. 5, the fluorescence observation unit 3 includes an image-acquisition element 23 that captures an image of the light reflected by the mirror 22. In the figure, reference sign 24 denotes a mirror.

The image-acquisition element 23 is connected to the controller 26. The memory stores a camera-observation image acquired by the image-acquisition element 23.

With this configuration, in a state in which the dichroic mirror 12 is disposed on the optical axis S of the objective lens 15 by actuating the insertion/retraction mechanism, it is possible to irradiate the sample X with the ultrashort pulsed laser light and to detect the fluorescence, as described above. On the other hand, in a state in which the mirror 22 is disposed on the optical axis S of the objective lens 15 by actuating the insertion/retraction mechanism, by stopping the irradiation with the ultrashort pulsed laser light and by irradiating the sample X with white light from outside the fluorescence observation unit 3, the reflected light from the sample X collected by the objective lens 15 is reflected by the mirrors 22 and 24, and an image of the reflected light is captured by the image-acquisition element 23. In this way, it is possible to acquire the camera-observation image of the surface of the sample X.

By acquiring the camera-observation image of the surface of the sample X, by positioning the fluorescence observation unit 3 with respect to the sample X, while confirming the observation position by displaying the acquired camera-observation image on the monitor 27, and by irradiating the sample X with the ultrashort pulsed laser light from the light source 2, with the dichroic mirror 12 being inserted by actuating the insertion/retraction mechanism, it is possible to acquire a bright fluorescence image.

Although the fluorescence split off by the dichroic mirror 12 is guided to the photomultiplier tube 4 through the second optical fiber 6 in this embodiment, instead, the photomultiplier tube 4 may be fixed to the housing 8, and the fluorescence may be detected by the photomultiplier tube 4, without passing through the optical fiber 6.

Similarly, although the reflected light from the surface of the sample X, deflected by the mirror 22, is deflected by the mirror 24, instead, an image of the reflected light may be directly captured by the image-acquisition element 23 after the reflected light is deflected by the mirror 22.

The following aspects of the invention are derived from the above-described embodiments and modifications thereof.

A first aspect of the present invention is a fluorescence observation unit including: a scanner that scans ultrashort pulsed laser light from a light source; a pupil projection lens that focuses the ultrashort pulsed laser light scanned by the scanner; an image-forming lens that converts the ultrashort pulsed laser light, focused by the pupil projection lens, to substantially collimated light and causes the ultrashort pulsed laser light to be incident on an objective lens; and a dichroic mirror that splits off, from the optical path of the ultrashort pulsed laser light, fluorescence that is generated at a light-focusing position as a result of the ultrashort pulsed laser light being focused on a sample by the objective lens and is collected by the objective lens. The image-forming lens includes a first optical system having positive refractive power and disposed adjacent to the objective lens, and a second optical system having negative refractive power and disposed at a position closer to the pupil projection lens than the first optical system is. The dichroic mirror is disposed between the first optical system and the second optical system.

According to the first aspect of the present invention, the ultrashort pulsed laser light from the light source is scanned by the scanner, is focused by the pupil projection lens, is converted into substantially collimated light by image-forming lens, and is made incident on the objective lens. The ultrashort pulsed laser light entering the objective lens is focused on the sample disposed at the focal position of the objective lens, and the photon density is increased at this light-focusing position. As a result, a fluorescent substance existing in the sample is excited, and fluorescence is generated.

The fluorescence generated at the focal position of the objective lens scatters in all directions in the sample, and only the fluorescence emitted from the surface of the sample in the direction in which the fluorescence enters the objective lens is collected by the objective lens. Thereafter, the fluorescence is converted to converging light by the first optical system, which has positive refractive power and constitutes the image-forming lens, and fluorescence entering the first optical system from outside the optical axis is also split off from the optical path of the ultrashort pulsed laser light by the dichroic mirror, in a state being refracted toward the optical axis direction.

Specifically, when the light-focusing position of the ultrashort pulsed laser light on the sample is moved by the scanner, the fluorescence beam emitted from the focal position and collected by the objective lens fluctuates around the pupil position of the objective lens. However, by allowing the fluorescence to pass through the first optical system having positive refractive power, it is possible to reduce the amount of fluctuation.

Furthermore, the fluorescence entering the objective lens from a relatively wide area around the focal position is also converted to converging light having a smaller diameter by passing through the first optical system having positive refractive power and is split off from the optical path of the ultrashort pulsed laser light by the dichroic mirror.

Hence, it is possible to split off, with the dichroic mirror, the fluorescence that cannot be split off in the form of a collimated light beam emitted from the objective lens and to efficiently detect the fluorescence. Thus, even when the ultrashort pulsed laser light is focused at a deeper position in the sample, a bright and sharp fluorescence image can be acquired.

According to the first aspect of the present invention, the fluorescence observation unit may further include an astigmatism correcting plate between the first optical system and the second optical system.

Because the fluorescence between the first optical system and the second optical system is converging light due to the first optical system having positive refractive power, the light beam is shifted only in the inclination direction of the dichroic mirror due to the refraction occurring when the ultrashort pulsed laser light passes through the dichroic mirror disposed so as to be inclined in one direction with respect to the optical axis. By disposing an astigmatism correcting plate to shift the light beam in the direction opposite to the direction of the shift caused by the dichroic mirror, the shift of the light-focusing position of the ultrashort pulsed laser can be eliminated.

A second aspect of the present invention is a fluorescence observation apparatus including: the fluorescence observation unit according to the first aspect; and a photodetector that detects the fluorescence split off by the dichroic mirror.

According to the second aspect of the present invention, by detecting, with the photodetector, the converging light formed by focusing the fluorescence fluctuating with a small amount of fluctuation and scattered in a wide area around the light-focusing position of the ultrashort pulsed laser light on the sample, it is possible to acquire a bright and sharp fluorescence image at a deeper position in the sample.

In the second aspect of the present invention, the fluorescence observation apparatus may further include an optical fiber that connects the fluorescence observation unit and the photodetector, and the fluorescence observation unit may include a coupling lens that focuses, at an end of the optical fiber, the fluorescence split off by the dichroic mirror.

With this configuration, by fixing the photodetector somewhere outside the fluorescence observation unit and by bending the optical fiber, it is possible to move the fluorescence observation unit. Hence, it is possible to move the fluorescence observation unit while fixing the sample and to observe the various portions of the sample from various directions.

In the second aspect of the present invention, the fluorescence observation unit may include an optical-path deflecting member that deflects the fluorescence split off by the dichroic mirror in the direction parallel to the optical axis of the objective lens and causes the fluorescence to be incident on the coupling lens.

With this configuration, it is possible to deflect the optical path of the fluorescence, focused by the coupling lens, with the optical-path deflecting member and to cause the fluorescence to be incident on the optical fiber disposed in the direction parallel to the optical axis of the objective lens. In other words, it is possible to extend the optical fiber from the fluorescence observation unit in the direction parallel to the optical axis of the objective lens. As a result, even when the fluorescence observation unit is swiveled about the axis intersecting the optical axis near the focal position of the objective lens, the optical fiber does not inhibit such a movement, and it is possible to make the space around the objective lens compact and to ensure a large swiveling angle.

In the second aspect of the present invention, the fluorescence observation apparatus may further include a relay lens that relays, to the photodetector, the fluorescence guided by the optical fiber and emitted from the other end the optical fiber.

With this configuration, although the fluorescence entering one end of the optical fiber and guided by the optical fiber diverges at a predetermined divergence angle when emitted from the other end of the optical fiber, the fluorescence is converted to substantially collimated light by the relay lens, is focused again, and is made incident on the photodetector. The projection magnification of the relay lens from the other end of the optical fiber to a light-receiving surface of the photodetector is set such that the diameter of the fluorescence beam entering the photodetector is within the effective area of the light-receiving surface of the photodetector and such that the incident numerical aperture (incident NA) to the photodetector is within an allowable range of the photodetector. Thus, it is possible to efficiently detect the fluorescence, without being influenced by the dependence of the photodetector on the angle and the entrance position.

In the second aspect of the present invention, the relay lens may convert the fluorescence emitted from the other end of the optical fiber to a substantially collimated light beam, and the fluorescence observation apparatus may include a light-splitting dichroic mirror that splits the substantially collimated light beam, converted by the relay lens, according to the wavelength; and a plurality of the photodetectors that detect the fluorescences split by the light-splitting dichroic mirror, respectively.

With this configuration, the fluorescence is split according to the wavelength by the light-splitting dichroic mirror disposed in the collimated light beam portion formed by the relay lens and is detected by different photodetectors. Thus, it is possible to acquire a bright and sharp fluorescence image with each wavelength.

In the second aspect of the present invention, the fluorescence observation unit may include a housing in which the scanner, the pupil projection lens, the image-forming lens, and the dichroic mirror are mounted, and the photodetector may be fixed to the housing.

With this configuration, it is possible to detect the fluorescence split off by the dichroic mirror with the photodetector directly or via a few optical elements, without using the optical fiber. Thus, it is possible to reduce the loss of the fluorescence occurring every time the fluorescence passes through an optical element and to acquire a brighter fluorescence image.

In the second aspect of the present invention, the fluorescence observation unit may include an observation-light deflecting member that deflects the light from the sample, collected by the objective lens, in a direction different from the direction of the dichroic mirror; an image-acquisition element that acquires an image of the light deflected by the observation-light deflecting member; and an insertion/retraction mechanism that alternatively disposes the dichroic mirror and the observation-light deflecting member in the optical path of the ultrashort pulsed laser light.

With this configuration, by actuating the insertion/retraction mechanism and disposing the dichroic mirror in the optical path of the ultrashort pulsed laser light between the first optical system and the second optical system, it is possible to split off, with the dichroic mirror, the fluorescence collected by the objective lens and further focused by the first optical system from the optical path of the ultrashort pulsed laser light and to detect the fluorescence with the photodetector. On the other hand, by actuating the insertion/retraction mechanism and disposing the observation-light deflecting member in the optical path of the ultrashort pulsed laser light between the first optical system and the second optical system, it is possible to deflect, with the observation-light deflecting member, the light from the sample collected by the objective lens and further focused by the first optical system in another direction and to acquire an image of the light with the image-acquisition element. Thus, for example, it is possible to acquire an image of the surface of the sample to confirm the observation position and then switch to the dichroic mirror to observe the fluorescence image.

In the second aspect of the present invention, the fluorescence observation apparatus may further include swiveling mechanism that causes the fluorescence observation unit to swivel about an axis intersecting the optical axis of the objective lens near the focal position of the objective lens.

With this configuration, by actuating the swiveling mechanism, it is possible to change the direction of the optical axis of the objective lens while substantially fix the focal position of the objective lens on the sample and to observe the sample from various directions, while fixing the sample.

In the second aspect of the present invention, the optical fiber may be a multi-mode fiber.

In the second aspect of the present invention, the optical fiber may be a liquid fiber.

With this configuration, by using the multi-mode fiber having a large core, in particular, by using the liquid fiber, it is possible to reduce the loss of the fluorescence fluctuating with a small amount of fluctuation, the loss occurring when entering the optical fiber, and to cause the fluorescence to be efficiently incident on the photodetector.

In the second aspect of the present invention, the fluorescence observation apparatus may further include a light-source optical fiber that connects the light source for generating the ultrashort pulsed laser light and the fluorescence observation unit and guides the ultrashort pulsed laser light emitted from the light source to the fluorescence observation unit.

With this configuration, by also fixing the light source for generating the ultrashort pulsed laser light somewhere outside the fluorescence observation unit and by bending the light-source optical fiber, it is possible to easily move the fluorescence observation unit and to observe the sample from various positions, while fixing the sample.

REFERENCE SIGNS LIST 1 fluorescence observation apparatus
2 light source
3 fluorescence observation unit
4, 4a, 4b, and 4c photomultiplier tube (photodetector)
5 first optical fiber (light-source optical fiber)
6 second optical fiber (optical fiber)
7 relay optical system (relay lens)
8 housing
9 scanner
10 pupil projection lens
11 image-forming lens
12 dichroic mirror
13, 24 mirror (optical-path deflecting member)
14 coupling lens
15 objective lens
17 first optical system
18 second optical system
20 light-splitting dichroic mirror
21 astigmatism correcting plate
22 mirror (observation-light deflecting member)
23 image-acquisition element
X sample
S optical axis

The invention claimed is:
1. A fluorescence observation unit comprising:
   a scanner that scans ultrashort pulsed laser light from a light source;
   a pupil projection lens that focuses the ultrashort pulsed laser light scanned by the scanner;
   an image-forming lens that converts the ultrashort pulsed laser light, focused by the pupil projection lens, to substantially collimated light and causes the ultrashort pulsed laser light to be incident on an objective lens; and
   a dichroic mirror that splits off, from the optical path of the ultrashort pulsed laser light, fluorescence that is generated at a light-focusing position as a result of the ultrashort pulsed laser light being focused on a sample by the objective lens and is collected by the objective lens, wherein
   the image-forming lens includes a first optical system having positive refractive power and disposed adjacent to the objective lens, and a second optical system having negative refractive power and disposed at a position closer to the pupil projection lens than the first optical system is, and
   the dichroic mirror is disposed between the first optical system and the second optical system.

2. The fluorescence observation unit according to claim 1, further comprising an astigmatism correcting plate between the first optical system and the second optical system.

3. A fluorescence observation apparatus comprising:
   the florescence observation unit according to claim 1; and
   a photodetector that detects the fluorescence split off by the dichroic mirror.

4. The fluorescence observation apparatus according to claim 3, further comprising an optical fiber that connects the fluorescence observation unit and the photodetector, wherein
   the fluorescence observation unit includes a coupling lens that focuses, at an end of the optical fiber, the fluorescence split off by the dichroic mirror.

5. The fluorescence observation apparatus according to claim 4, wherein the fluorescence observation unit includes an optical-path deflecting member that deflects the fluorescence split off by the dichroic mirror in the direction parallel to the optical axis of the objective lens and causes the fluorescence to be incident on the coupling lens.

6. The fluorescence observation apparatus according to claim 4, further comprising a relay lens that relays, to the photodetector, the fluorescence guided by the optical fiber and emitted from the other end of the optical fiber.

7. The fluorescence observation apparatus according to claim 6, wherein
   the relay lens converts the fluorescence emitted from the other end of the optical fiber to a substantially collimated light beam, and
   the fluorescence observation apparatus includes a light-splitting dichroic mirror that splits the substantially collimated light beam, converted by the relay lens, according to the wavelength; and a plurality of the photodetectors that detect fluorescences split by the light-splitting dichroic mirror, respectively.

8. The fluorescence observation apparatus according to claim 3, wherein
   the fluorescence observation unit includes a housing in which the scanner, the pupil projection lens, the image-forming lens, and the dichroic mirror are mounted, and
   the photodetector is fixed to the housing.

9. The fluorescence observation apparatus according to claim 3, wherein the fluorescence observation unit includes an observation-light deflecting member that deflects the light from the sample, collected by the objective lens, in a direction different from the direction of the dichroic mirror; an image-acquisition element that acquires an image of the light deflected by the observation-light deflecting member; and an insertion/retraction mechanism that alternatively disposes the dichroic mirror and the observation-light deflecting member in the optical path of the ultrashort pulsed laser light.

10. The fluorescence observation apparatus according to claim 3, further comprising a swiveling mechanism that causes the fluorescence observation unit to swivel about an axis intersecting the optical axis of the objective lens near the focal position of the objective lens.

11. The fluorescence observation apparatus according to claim 4, wherein the optical fiber is a multi-mode fiber.

12. The fluorescence observation apparatus according to claim 11, wherein the optical fiber is a liquid fiber.

13. The fluorescence observation apparatus according to claim 3, further comprising a light-source optical fiber that connects the light source for generating the ultrashort pulsed laser light and the fluorescence observation unit and guides the ultrashort pulsed laser light emitted from the light source to the fluorescence observation unit.

* * * * *